United States Patent [19]

Matsumoto et al.

[11] Patent Number: 5,410,038
[45] Date of Patent: Apr. 25, 1995

[54] METHOD OF PREPARING D-ALTROSE

[75] Inventors: Katsuya Matsumoto; Takashi Ebata; Hajime Matsushita, all of Yokohama, Japan

[73] Assignee: Japan Tobacco Inc., Tokyo, Japan

[21] Appl. No.: 849,387

[22] PCT Filed: Oct. 9, 1991

[86] PCT No.: PCT/JP91/01376

§ 371 Date: May 12, 1992

§ 102(e) Date: May 12, 1992

[87] PCT Pub. No.: WO92/06986

PCT Pub. Date: Apr. 3, 1992

[30] Foreign Application Priority Data

Oct. 12, 1990 [JP] Japan .................. 2-272186

[51] Int. Cl.⁶ .................. C07H 1/00; C07H 3/02
[52] U.S. Cl. .................. 536/124; 536/1.11
[58] Field of Search .................. 536/124, 1.1

[56] References Cited

U.S. PATENT DOCUMENTS 3,304,298  2/1967  Iwai et al. .................. 536/124
4,760,139  7/1988  Feniou et al. .................. 536/18.5
4,824,943  4/1989  Hroii et al. .................. 536/124

OTHER PUBLICATIONS

T, Mukaiyama et al., Chem. Lett., pp. 173 (1983).
Brimacombe et al. (1978) *Carbohydrate Research* 60:C11–C12.
Singh et al. (1971) *Canadian Journal of Chemistry* 49:1179–1186.
Bock et al. (1980) *Acta Chemica Scandinavica* B34:389.
Shafizadeh et al. (1977) *Carbohydrate Research* 58:79–87.
Levene et al. (1910) Ber, 43, 3141–3147.
Richtmyer et al. (1935) *J. Am. Chem. Soc.* 57:1716–1721.
N. Richtmyer (1962) Methods in Carboxylate Chemistry, 1:107–113.
"Bulletin of the Chemical Society of Japan" vol. 64 No. 7-1991.

*Primary Examiner*—David A. Redding
*Assistant Examiner*—Everett White

[57] ABSTRACT

Disclosed is a method of preparing D-altrose (4) from the starting material levo-glucosenon (1) in accordance with reactions denoted by reaction formulas (I), (II) and (III) given below:

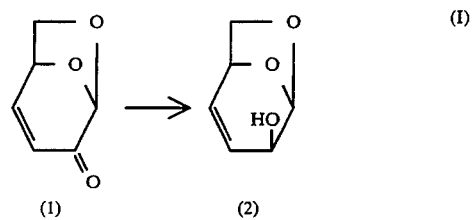

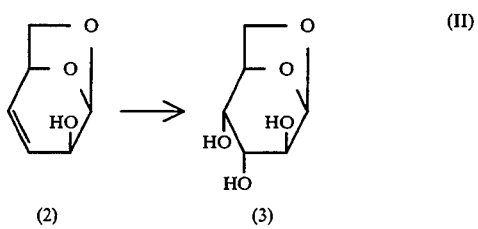

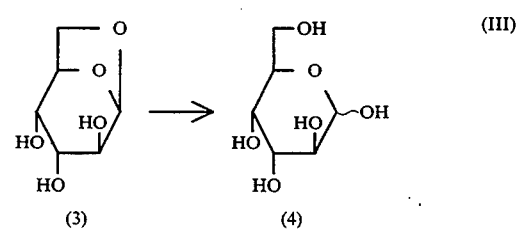

11 Claims, 1 Drawing Sheet

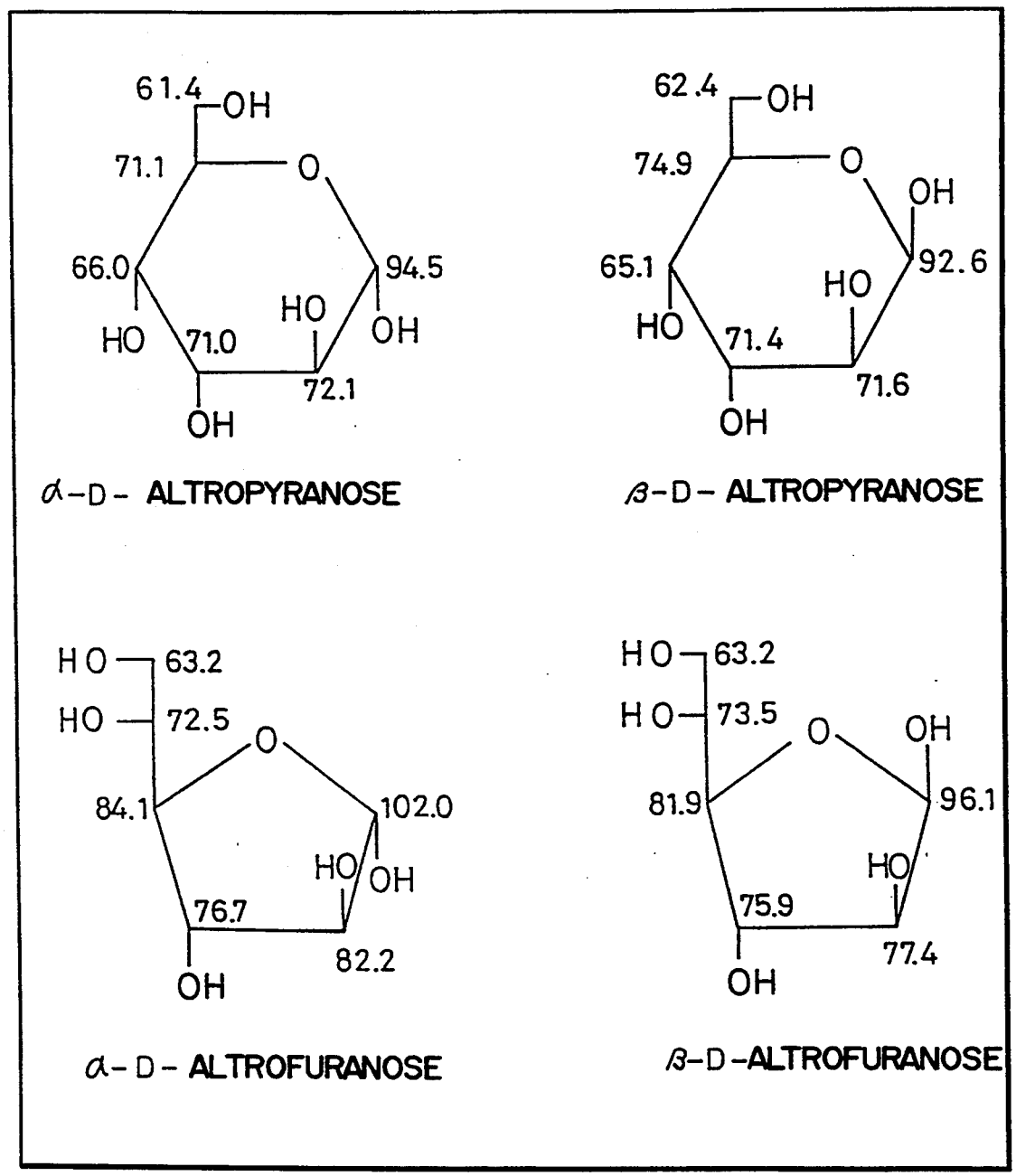
F I G. 1

METHOD OF PREPARING D-ALTROSE

TECHNICAL FIELD

The present invention relates to a method of preparing D-altrose, which is a rare sugar, more particularly, to a method of preparing D-altrose from levoglucosenone.

PRIOR ART

D-altrose is a pyranose type aldohexose represented by structural formula (4) given below. The D-altropyranose (4) is in equilibrium with D-altrofuranose (6) via a ring-opened aldohexose (5) as an intermediate. It should also be noted that each of pyranose (4) and furanose (6) has α- and β-anomers. In other words, D-altrose is present as an equilibrium mixture of these plurality of anomers.

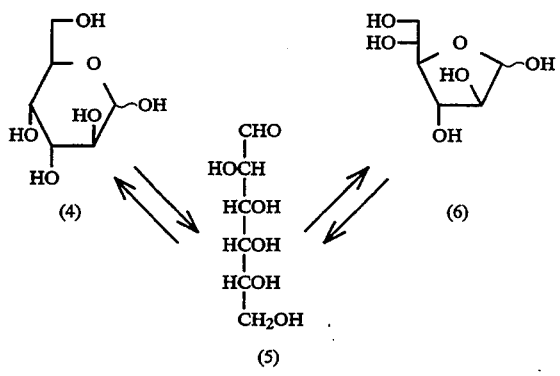

D-altrose is a rare sugar, which is present in nature in an extremely small amount. Altrose presently available on the market is a synthetic substance produced by, for example, Aldrich Inc. Naturally, altrose available on the market is markedly costly, compared with sugars present in nature in large amounts such as glucose. For example, the prices of altrose available on the market at present as a reagent are given below:

$62.40 (100 mg) for altrose produced by Aldrich Inc.

21,400 (100 mg) for altrose produced by Junsei Kagaku Inc.

Recently, sugar chains such as oligosaccharides and polysaccharides, which perform functions useful as a physiologically active substance, have attracted attention in the field of fine chemicals such as medicines and agricultural chemicals. Presently, the objects of researches on the sugar chain are restricted to those consisting of monosaccharides present in nature in large amounts and readily available to researchers, such as D-glucose, D-mannose and D-galactose. However, it is expected that various monosaccharides other than those present in nature will be required in the future in research on the synthesis of sugar chains performing more useful functions. Under the circumstances, it is highly significant and necessary to develop a method which permits preparing D-altrose, which is a rare sugar difficult to obtain, in high yield while diminishing the number of treating steps.

Various methods were proposed in the past in an attempt to synthesize D-altrose. For example, a method of synthesizing D-altrose based on the Kiliani-Fischer method, in which D-ribose is converted into D-altronic acid and, then, into D-altrose, is described in "P. A. Leven and W. A. Jacobs, Ber., 43, 3141 (1910)". In this method, however, involved is a reaction in which the 1-position of D-ribose is converted to cyanohydrin. Since this reaction is not stereoselective, D-allonic acid, which is a C-2 epimer of D-altronic acid, is also generated as a by-product, in addition to D-altronic acid which is an intermediate product generated in the synthesis of D-altrose. Thus, it is necessary to employ fractional crystallization in order to isolate D-altronic acid, with the result that the product yield is as low as only 3%.

Another method is described in, for example, "N. K. Richtmyer, C. S. Hudson, J, Am. Chem. Soc., 57, 1716 (1935)". In this method, the 2- and 3-positions of the D-glucose portion included in lactose are subjected to walden inversion so as to obtain neolactose consisting of D-altrose and D-galactose, followed by hydrolyzing neolactose so as to obtain the desired D-altrose product. The D-galactose contained in the mixture obtained after the hydrolysis is consumed by allowing yeast to act thereon and, thus, is removed. The remaining D-altrose is refined as a benzyl mercaptal derivative and, then, returned to D-altrose. It should be noted that this method necessitates a step of protecting the hydroxyl group which is irrelevant to the reaction and another step of releasing the protective group after the reaction. It follows that as many as eight steps are involved in this method starting with the Walden inversion of lactose. Naturally, troublesome operations are required for synthesizing the product D-altrose. In addition, the product yield is as low as only 8%.

Still another method of synthesizing D-altrose is described in, for example, "Methods in Carbohydrate Chemistry" Vol. I, Academic Press, New York and London, p. 107 (1962). In this method, D-glucose, which is used as the starting material, is converted first into its 2,3-epoxy derivative and, then, the steric configuration of the hydroxyl groups in the 2- and 3-positions is inverted. In this method, it is also necessary to employ the steps of protecting the hydroxyl group, releasing the protective group, and the refining step. It follows that this method also comprises as many as eight steps starting with the treatment of the starting material glucose. In addition, the product yield is as low as only 9%.

DISCLOSURE OF THE INVENTION

The present invention is intended to overcome the above-noted difficulties inherent in the prior art, and provides a method of preparing D-altrose, which permits the production of D-altrose in high yield and also permits a reduction in the number of treating steps.

The present invention is described as a method of manufacturing D-altropyranose represented by structural formula (4) referred to previously. As described previously, D-altropyranose (4) is in equilibrium mixture with the ring-opened D-aldohexose (5) and D-altrofuranose (6), each of isomers (4) and (6) having α- and β-anomers. Naturally, it is reasonable to interpret the present invention to include the method of preparing these isomers and anomers, too.

As a result of an extensive research made in an attempt to achieve the object described above, the present inventors have arrived at an effective method of preparing D-altrose, which permits preparing D-altrose in high yield by using levoglucosenone as a starting material. In the method reached by the present inventors, it is unnecessary to employ troublesome operations such as introduction of a protective group and fractional crystallization, making it possible to prepare the desired D-altrose by only three steps.

According to the present invention, there is provided a method of preparing D-altrose, essentially comprising the steps of:

a) selectively reducing the carbonyl group of levoglucosenone having the structural formula (1) given below into a β-hydroxyl group so as to obtain a compound having the structural formula (2) given below, as shown in reaction formula (I) below:

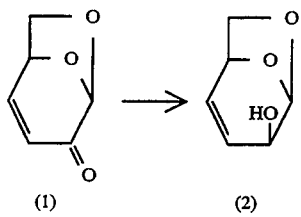

b) performing cis-addition of two α-hydroxyl groups to the double bond included in compound (2) so as to obtain a compound having the structural formula given below, as shown in reaction formula (II) below:

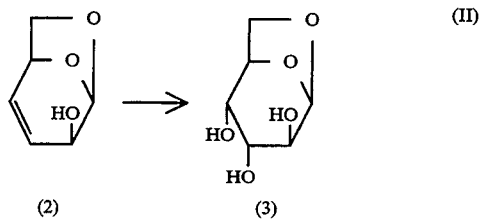

and c) hydrolyzing the 1,6-anhydro bond of compound (3) in the presence of an acid catalyst, as shown in reaction formula (III) below, so as to obtain D-altrose having the structural formula (4) given below:

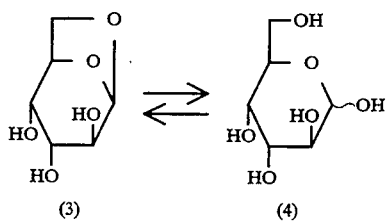

Levoglucosenone (1) used as a starting material step a) given above can be obtained easily at low cost by thermal decomposition of cellulose, as described in, for example, "Carbohydrate Research, 58, 78–87 (1977)". Levoglucosenone obtained by the method of thermal decomposition described in this reference can be used as the starting material in the present invention.

In the first step, the carbonyl group of levoglucosenone (1) is converted into a β-OH group, as shown in reaction formula (1). It is possible to carry out the reduction reaction by using a hydride reagent such as lithium aluminum hydride or sodium borohydride. In the case of using lithium aluminum hydride, levoglucosenone is mixed with lithium aluminum hydride in a suitable solvent such as diethyl ether, preferably at a low temperature e.g., temperatures lower than 0° C. After the mixing, the reduction reaction is carried out at about room temperature for 1 to 12 hours. After the reaction, the reaction mixture is washed with a suitable solvent such as methanol, followed by removing ingredients by means of filtration and subsequently removing the solvent by means of distillation. The residue is then refined with a suitable column chromatograph using, for example, silica gel so as to obtain a white powdery compound (2). A mixed solvent consisting of, for example, a 1:1 mixture of hexane and diethyl ether can be used as an eluent for the column chromatograph. The white powdery reaction product is recrystallized by using a suitable solvent so as to obtain white crystals of the compound (2), i.e., 1,6-anhydro-3,4-dideoxy-β-D-threo-hex-3-enopyranose. In general, the product yield in this step is at least 70%.

In step b) employed in the present invention, two α-OH groups are added in a cis-configuration with respect to the double bond formed between 3-position and 4-position of the compound (2) obtained in step a) described above, as shown in reaction formula (II). This reaction can be performed by oxidizing the compound (2) with osmium tetroxide or a permanganate. The stereoselectivity of the two OH groups added in this reaction is substantially complete in any of these reactions.

In the case of using osmium tetroxide, the reaction between the compound (2) and N-methylmorpholine-N-oxide acting as an oxidizing agent is carried out, by using osmium tetroxide as a catalyst, at room temperature for about 13 hours within a mixed solvent consisting of 8 parts of acetone and 1 part of water. The amount of the oxidizing agent should be at least two times as much as that of the compound (2). Also, the reaction should be carried out in the presence of osmium tetroxide acting as a catalyst. The amount of the catalyst should be 0.1 to 1 times as much as that of the compound (2). Then, sodium sulfite or sodium pyrosulfite is added to the reaction system so as to treat the osmium tetroxide, followed by removing the solvent by means of distillation under reduced pressure. In the next step, the distillation residue is washed with hot ethanol, followed by filtration. The filtrate is then distilled under a reduced pressure so as to remove the solvent. The residue is refined by means of silica gel column chromatograph so as to obtain a white powdery reaction product. It is possible to use a mixed solvent consisting of dichloroethane and acetone as an eluent for the column chromatograph. The mixing ratio of dichloroethane to acetone should desirably fall within a range of between 1:2 and 1:4. Further, the reaction product is recrystallized from ethanol or 2-propanol so as to obtain white crystals of compound (3), i.e., 1,6-anhydro-β-D-altropyranose (D-altrosan). In general, the product yield in this step is 73 to 86%.

In step c), the 1,6-anhydro bond in the acetal portion of the compound (3) obtained in step b) is subjected to hydrolysis so as to obtain the desired D-altrose (4), as shown in reaction formula (III). The hydrolysis can be performed within an acidic aqueous solution using an ordinary acid catalyst such as hydrochloric acid, sulfuric acid, or a cation exchange resin (proton type). It is desirable to set the acid concentration at about 1N. Also, it is desirable to use hydrochloric acid as the acid catalyst.

To be more specific, the compound (3) put in the acidic solution noted above is kept stirred for 5 to 70 hours at 40° to 100° C. It is desirable to add dioxane to the aqueous solution. The volume ratio of the acidic solution to dioxane should desirably fall within a range of between 2:0 and 2:1. Since the reaction (III) is an equilibrium reaction between the compound (3) and compound (4), i.e., reaction product in step c), the unreacted raw material compound (3) is recovered together with the compound (4). Thus, the reaction mixture is passed through an anion exchange resin (hydroxy anion type) so as to neutralize the reaction mixture, followed by removing the solvent from the reaction mixture by means of distillation under reduced pressure. Further, the oily residue is passed through a silica gel column chromatograph so as to separate the residue into the formed product (4) and the raw material compound (3). It is possible to use, as an eluent in the column chromatograph, a solvent mixture consisting of chloroform and methanol or a solvent mixture consisting of dichloromethane and methanol, the mixing ratio desirably ranging between 5:1 and 1:1. It is possible to obtain white crystals of the compound (4) by drying, under reduced pressure, a fraction of the oily compound (4) eluted later. On the other hand, the unreacted raw material compound (3) which is eluted first, is used again as the raw material compound in step c).

Where step c) is performed only once, it is possible to obtain the desired compound (4) in a yield of about 11 to 25% based on the raw material compound (3) used, and about 24 to 68% based on the reacted compound (3). It is also possible to recover about 54 to 67% of the unreacted compound (3). Where step c) is repeated three times, the desired compound (4) can be obtained in a yield of about 39% based on the raw material compound (3) used, and about 48% based on the reacted compound (3). Further, about 19% of the unreacted compound (3) can be recovered in the final operation of step c).

The product obtained in step c) has been found to be the desired D-altrose (4) by measurement of the $^{13}$C-NMR spectrum. To be more specific, the $^{13}$C-NMR spectrum of the product noted above has been found to be consistent with the values reported in the literature given below:

1 E Breitmaier, W. Voelter, "Carbon-13 NMR Spectroscopy", Third completely revised edition, pp. 380 to 383 (1987));
2. A. S. Perlin and B. Casu, Can. J. Chem., 53, 1212 (1975)"; and
3. G. J. Wolff, Thesis. Bonn (1979)

D-altrose identified by the $^{13}$C-NMR spectrum noted above is a mixture of four kinds of isomers shown in FIG. 1. The numerals shown in FIG. 1 denote the chemical shifts of the carbon atoms. The presence of the ring-opened D-aldose (5) was not recognized. It is considered reasonable to understand that, since the stability of each of pyranose (4) and furanose (6) is markedly higher than that of the ring-opened D-aldose (5), D-aldose (5) in the ring-opened state is present for only very short time, resulting in failure to recognize the presence of the ring-opened aldose (5).

BRIEF DESCRIPTION OF THE DRAWING

FIG. 1 shows the chemical structures of four isomers of D-altrose synthesized by the method of the present invention as well as the chemical shifts of the carbon atoms confirmed by $^{13}$C-NMR spectroscopy.

BEST MODE OF THE INVENTION

The present invention will be described in more detail with reference to the Examples which follow. Various physical data reported in the following Examples were obtained by the measurement with the apparatus listed below:

Melting point: MRK photoelectric automatic melting point measuring apparatus;
Specific rotation: JASCO DIP-370
IR: JASCO FT/IR-5000
NMR: Bruker AM-300

Example 1

<Step a>

Synthesis of 1,6-anhydro-3,4-dideoxy-$\beta$-D-threo-hex-3-enopyranose (compound 2):

2.42 g (63.8 mmol) of lithium almunium hydride was added to 200 ml of dry ether to prepare a hydride solution, followed by adding dropwise a solution prepared by dissolving 7.98 g (63.3 mmol) of levoglucosenone in 130 ml of dry ether into the hydride solution while cooling the hydride solution in an ice water bath. After completion of the addition, the resultant solution was kept stirred at room temperature for an hour, followed by further adding dropwise 4.60 g (256 mmol) of water to the solution. Then, methanol was added to the reaction mixture, followed by removing the insoluble components by means of filtration. Further, the solvent was removed from the filtrate by means of distillation under reduced pressure, followed by refining the residue by means of a silica gel column chromatograph. A mixed solvent consisting of hexane and diethyl ether was used as an eluent for the column chromatograph. The mixing ratio of hexane to diethyl ether fell within a range of between 1:1 and 1:2. Finally, the formed product was recrystallized from a mixed solvent consisting of 4 parts of hexane and 1 part of diethyl ether so as to obtain 5.70 g of 1,6-anhydro-3,4-dideoxy-$\beta$-D-threo-hex-3-enopyranose (compound 2). The product yield was 70.3%. The physical data of the formed product were found to be as follows:

Melting Point: 65.6 to 66.4° C. $[\alpha]^{25}$: $-30.3°$ (c=1.00, CHCl$_3$)
IR ($\nu_{max}$): 3412(br), 3050(w), 1425(m), 1259(m), 1180(m), 1125(s), 1071(s), 1046(s)
$^1$H-NMR (CDCl$_3$, ppm from TMS): 2.10 (1H, d, J=12.0 Hz; OH), 3.74–3.78 (1H, dd, J=4, 1, 6.6 Hz; 6-position), 3.84 (1H, d, J=6.6 Hz; 6-position), 4.34 (1H, md, J=12.0 Hz; 2-position), 4.67 (1H, dd, J=4.1, 4.2 Hz; 5-position), 5.52 (1H, b; 1-position), 5.72 (1H, ddd, J=2.2, 2.2, 9.9 Hz; 3-position) 6.12 (1H, dd, J=4.2, 9.9 Hz; 4-position), <Step b>

Synthesis of 1,6-anhydro-$\beta$-D-altropyranose (D-altrosan; compound 3)

3.84 g (30.0 mmol) of the compound (2) obtained in step a), 0.76 g (3.0 mmol) of osmium tetroxide, and 7.03 g (60.0 mmol) of N-methyl morpholin-N-oxide were dissolved in a mixed solvent consisting of 8 parts of acetone and 1 part of water, and the resultant solution was kept stirred at room temperature for 13 hours. Then, 81.0 g (643 mmol) of sodium sulfite was added to the reaction system, followed by removing the solvent by distillation under reduced pressure. Further, hot ethanol was added to the residue to wash the residue, followed by filtration and subsequent distillation of the filtrate under reduced pressure so as to remove the ethanol. The residue after the distillation was refined by means of a silica gel column chromatograph. A mixed solvent consisting of methylene chloride and acetone was used as an eluent for the column chromatograph. The mixing ratio of methylene chloride to acetone fell within a range of between 1:2 and 1:4. Finally, the formed product was recrystallized from 2-propanol so as to obtain 4.19 g of 1,6-anhydro-β-D-altropyranose (D-altrosan; compound 3). The product yield was 86.0%. The physical data of the formed product were found to be as follows:

Melting Point: 129° to 130° C. $[\alpha]^{25}$: $-219°$ (c=1.00, H$_2$O)

IR ($\nu_{max}$): 3400(br), 1450(br), 1137(s), 1073(s), $^1$H-NMR (CD$_3$OD, ppm from CD$_3$OD, CD$_3$: 3.40 ppm): 3.75–3.83 (2H, m; 6-position), 3.61 (1H, dd, J=1.7, 8.6 Hz; 2-position), 3.69 (1H, dd, J=4.4, 8.6 Hz; 3-position), 3.89 (1H, dd, J=2.5, 4.4 Hz; 4-position), 4.61 (1H, ddd, J=2.1, 2.5, 4.6 Hz; 5-position), 5.30 (1H, d, J=1.7 Hz; 1-position), $^{13}$C-NMR (D$_2$O, ppm from 1,4-dioxane (67.4 ppm)): 102.0, 77.8, 72.9, 70.4, 70.0, 66.1

<Step C>

Synthesis of D-altrose (compound 4)

1.62 g (10.0 mmol) of the compound (3) obtained in step b) was dissolved in 100 ml of 1N hydrochloric acid, followed by adding 50 ml of dioxane to the resultant solution. The solution thus prepared was kept stirred for 5 hours at 100° C. The reaction mixture was then passed through an anion exchange resin (hydroxyl ion type Amberlit IRA-410) for neutralizing purposes, followed by removing the solvent by distillation under a reduced pressure. Further, the residue was passed through a silica gel chromatograph so as to separate the residue into the compound (3) used as the raw material and the desired D-altrose product (compound 4).

Step c) described above was repeated three times so as to obtain 0.70 g of D-altrose and recover at the same time 0.32 g of the raw material compound (3). The yield of the product D-altrose was 48.2% with respect to the raw material recovery. The spectral data of the obtained products were as follows:

IR ($\nu_{max}$): 3300(br), 1065(br), $^{13}$C-NMR (D$_2$O, ppm from 1,4-dioxane (67.4 ppm)):

α-pyranose:
  94.5 (1-position), 72.1 (2-position),
  71.0 (3-position), 66.0 (4-position),
  71.1 (5-position), 61.4 (6-position)
β-pyranose:
  92.6 (1-position), 71.6 (2-position),
  71.4 (3-position), 65.1 (4-position),
  74.9 (5-position), 62.4 (6-position)
α-furanose:
  102.0 (1-position), 82.2 (2-position),
  76.6 (3-position), 84.1 (4-position),
  72.5 (5-position), 63.2 (6-position)
β-furanose:
  96.1 (1-position), 77.4 (2-position),
  75.9 (3-position), 81.9 (4-position),
  73.5 (5-position), 63.2 (6-position)

Example 2

The D-altrose product was prepared as in Example 1, except that potassium permanganate was used as an oxidizing agent in step b), as described below:

<Step b>

Synthesis of 1,6-anhydro-β-D-altropyranose (D-altrosan; compound 3)

128 mg (1.00 mmol) of the compound (2) obtained in step a) of Example 1 was dissolved in 2.0 ml of water, followed by adding 16.0 ml of a 0.6% aqueous solution of sodium hydroxide to the resultant solution. Further, 190 mg (1.20 mmol) of potassium permanganate was added bit by bit to the solution while stirring the solution at room temperature. The resultant solution was kept stirred at room temperature for 20 minutes, followed by adding dropwise bit by bit a 1N hydrochloric acid to the solution so as to neutralize the solution. Then, 10 the insoluble components were removed by filtration, followed by removing the solvent by distilling the filtrate under reduced pressure. Further, the residue was refined by means of a silica gel column chromatograph so as to obtain 53 mg of 1,6-anhydro-β-D-altropyranose (D-altrosan; compound 3). A mixed solvent consisting of methylene chloride and acetone was used as an eluent for the column chromatograph. The mixing ratio of methylene chloride to acetone fell within a range of between 1:2 and 1:4. The yield of the compound (3) was 32.7%. Further, the $^{13}$C-NMR spectrum of the formed product was as follows, which were equal to those of the compound (3) obtained in step b) of Example 1:

$^{13}$C-NMR (D$_2$O, ppm from 1,4-dioxane (67.4 ppm)) 102.0, 77.8, 72.9, 70.4, 70.0, 66.1

Example 3

The D-altrose product was prepared as in Example 1, except that sodium borohydride was used as a reducing agent in step a), as described below:

<Step a>

Synthesis of 1,6-anhydro-3,4-dideoxy-β-D-threo-hex-3-enopyranose (compound 2)

16.0 g (127 mmol) of levoglucosenone was dissolved in 700 ml of water, followed by adding 8.00 g (211 mmol) of sodium borohydride to! the solution. The resultant system was kept stirred at room temperature for 5 minutes. Then, 400 ml of acetone was added to the mixture, and solvent was removed by distillation under reduced pressure, followed by adding chloroform to the residue so as to remove insoluble components by means of filtration. The filtrate was distilled under reduced pressure so as to remove the solvent. Further, the residue was recrystallized from a mixed solvent consisting of 4 parts of hexane and 1 part of diethyl ether so as to obtain 5.55 g of 1,6-anhydro-3,4-dideoxy-β-D-threo-hex-3-enopyranose (compound 2). The yield of the compound 2 was 34.1%. Further, the mother liquor after the recrystallization was refined with a silica gel column chromatograph by using, as an eluent, a mixed solvent consisting of 1 part of hexane and 1 to 2 parts of ether, and recrystallization was achieved again using a mixed solvent consisting of 1 part of hexane and 3 parts of ethyl acetate so as to obtain 2.14 g of the compound (2). The total yield of the compound (2) was 7.69 g, i.e., 60.1%. The $^1$H-NMR spectrum of the compound (2) thus obtained was found to be as follows, which was equal to that of the compound (2) obtained in step a) of Example 1:

$^1$H-NMR (CDCl$_3$, ppm from TMS):
  2.10 (1H, d, J=12.0 Hz; OH),
  3.74–3.78 (1H, dd, J=4.1, 6.6 Hz; 6-position), 3.84 (1H, d, J=6.6 Hz; 6-position),
4.34 (1H, md, J=12.0 Hz; 2-position),
4.67 (1H, dd, J=4.1, 4.2 Hz; 5-position),
5.52 (1H, b; 1-position),
5.72 (1H, ddd, J=2.2, 2.2, 9.9 Hz; 3-position),
6.12 (1H, dd, J=4.2, 9.9 Hz; 4-posiiton), Example 4

The D-altrose product was prepared as in Example 1, except that sulfuric acid was used as an acid catalyst in step c), as follows:

<Step c>

Synthesis of D-altrose (compound 4)

0.16 g (1.00 mmol) of the compound (3) was dissolved in 5 ml of 1N sulfuric acid, and the resultant solution was kept stirred for 5 hours at 100° C. The reaction mixture was passed through an anion exchange resin (hydroxyl ion type amberlight IRA-410) for neutralizing purposes, followed by removing the solvent by means of distillation under reduced pressure. Formation of the desired compound of the present invention, i.e., D-altrose (compound 4), was confirmed by thin layer chromatography. It was also confirmed that the raw material compound (3) was mixed with the product compound (4). The mixing ratio of these compounds (3) and (4) was about 1:1.

Example 5

The product D-altrose was prepared as in Example 1, except that a cation exchange resin was used as an acid catalyst in step c), as follows:

<Step c>

Synthesis of D-altrose (compound 4)

0.16 g (1.00 mmol) of the compound (3) was dissolved in 50 ml of water, followed by adding 4.00 g of amberlight IR-120B (proton type cation exchange resin) to the resultant solution. The system thus prepared was kept stirred for 8.5 hours at 100° C. Then, the amberlight IR-120B was removed from the reaction system by means of filtration, followed by washing the cation exchange resin with water. Further, the solvent was removed from the filtrate and the washing water by means of distillation under reduced pressure. Formation of the desired compound of the present invention, i.e., D-altrose (compound 4), was confirmed by thin layer chromatography. It was also confirmed that the raw material compound (3) was mixed with the product compound (4). The mixing ratio of these compounds (3) and (4) was about 1:1.

As described above in detail, the method of the present invention makes it possible to obtain easily, stereospecifically and high yield D-altrose, which is one of the rare sugars present in the the nature in an extremely small amount, and which is difficult to obtain.

What is claimed is:

1. A method of preparing D-altrose, comprising the steps of:
  a) selectively reducing the carbonyl group of levoglucosenone of structural formula (1) to produce a β-hydroxyl group so as to obtain a compound having the structure of formula (2), shown in reaction scheme (I) below:

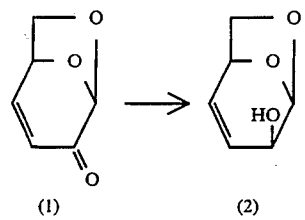

b) performing cis-addition of two α-hydroxyl groups to the double bond in compound (2) by employing osmium tetroxide as a catalyst so as to obtain a compound having the structural formula (3), shown in reaction scheme (II) below:

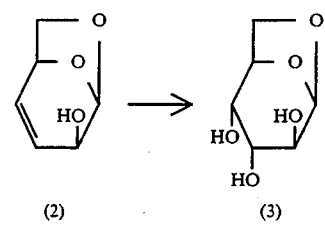

and
  (c) hydrolyzing the 1,6-anhydro bond in the acetal portion of compound (3) in the presence of an aqueous solution of an acid catalyst, as shown in reaction scheme (III) below, so as to obtain D-altrose of structural formula (4), shown below:

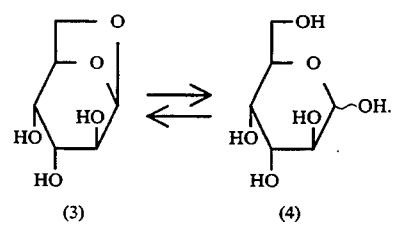

2. The method according to claim 1, wherein the reduction reaction in said step a) is carried out by using lithium aluminum hydride or sodium borohydride.

3. The method according to claim 2, wherein said levoglucosenone is mixed with said lithium aluminum hydride in diethyl ether at a temperature lower than 0° C., and said reduction reaction is carried out at about room temperature for 1 to 12 hours.

4. The method according to claim 1, wherein in said step b), said compound (2) is reacted with N-methylmorpholine-N-oxide at room temperature for about 13 hours in a mixed solvent consisting of 8 parts of acetone and 1 part of water.

5. The method according to claim 4, wherein the amount of said N-methylmorpholine-N-oxide is at least two times the amount of said compound (2).

6. The method according to claim 1, wherein the amount of said osmium tetroxide is 0.1 to 1 times the amount of said compound (2).

7. The method according to claim 1, wherein in step c), said acid catalyst is a member selected from the group consisting of hydrochloric acid, sulfuric acid, and a proton type cation exchange resin.

8. The method according to claim 7, wherein said acid catalyst is 1N hydrochloric acid.

9. The method according to claim 1, wherein in said step c), said compound (3) is stirred in the presence of said aqueous solution of said acid catalyst for 5 to 70 hours at 40° to 100° C.

10. The method according to claim 9, wherein dioxane is added to said aqueous solution of said acid catalyst.

11. The method according to claim 10, wherein the volume ratio of said aqueous solution of said acid catalyst to said dioxane is within the range of from 2:0 to 2:1.

* * * * *